United States Patent
Gettelman et al.

(10) Patent No.: US 9,629,573 B2
(45) Date of Patent: *Apr. 25, 2017

(54) INTERACTIVE VIRTUAL CARE

(71) Applicant: Accenture Global Services Limited, Dublin (IE)

(72) Inventors: Craig A. Gettelman, Chicago, IL (US); Dadong Wan, Palatine, IL (US); Ankur Pogula, Chicago, IL (US); Ben Reierson, Seattle, WA (US); Terrianne Erickson, Oak Lawn, IL (US)

(73) Assignee: ACCENTURE GLOBAL SERVICES LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,192

(22) Filed: May 24, 2016

(65) Prior Publication Data
US 2016/0262660 A1 Sep. 15, 2016

Related U.S. Application Data

(63) Continuation of application No. 14/842,519, filed on Sep. 1, 2015, now Pat. No. 9,370,319, which is a (Continued)

(51) Int. Cl.
| | |
|---|---|
| *A61B 5/103* | (2006.01) |
| *A61B 5/117* | (2016.01) |
| *A61B 5/11* | (2006.01) |
| *G06F 19/00* | (2011.01) |
| *G06T 7/00* | (2017.01) |
| *A61B 34/00* | (2016.01) |

(Continued)

(52) U.S. Cl.
CPC .............. *A61B 5/11* (2013.01); *A61B 5/0002* (2013.01); *A61B 5/0062* (2013.01); *A61B 5/0077* (2013.01); *A61B 5/112* (2013.01); *A61B 5/1118* (2013.01); *A61B 5/4803* (2013.01); *A61B 5/744* (2013.01); *A61B 34/25* (2016.02); *G06F 19/322* (2013.01); *G06F 19/3418* (2013.01); *G06F 19/3443* (2013.01); *G06T 7/0014* (2013.01); *A61B 3/0041* (2013.01); *A61B 5/6898* (2013.01); *A61B 2505/07* (2013.01); *G06T 2207/10021* (2013.01); *G06T 2207/10028* (2013.01); *G06T 2207/30004* (2013.01)

(58) Field of Classification Search
CPC ...................................................... A61B 5/00
USPC ................................ 600/300, 301, 587, 595
See application file for complete search history.

(56) References Cited

U.S. PATENT DOCUMENTS

| | | | | |
|---|---|---|---|---|
| 4,813,436 A | * | 3/1989 | Au ........................ | A61B 5/1038 356/620 |
| 5,231,483 A | * | 7/1993 | Sieber ..................... | G01S 3/807 348/169 |

(Continued)

FOREIGN PATENT DOCUMENTS

WO    WO2011/082346    7/2011

*Primary Examiner* — Rene Towa
*Assistant Examiner* — May Abouelela
(74) *Attorney, Agent, or Firm* — Mannava & Kang, P.C.

(57) ABSTRACT

An interactive virtual care system may include a user sensory module to acquire multi-modal user data related to user movement. A data analysis module may compare the multi-modal user data to predetermined historical user data and/or statistical norm data for users to identify an anomaly in the user movement.

20 Claims, 12 Drawing Sheets

Related U.S. Application Data continuation of application No. 14/513,960, filed on Oct. 14, 2014, now Pat. No. 9,149,209, which is a continuation of application No. 14/293,562, filed on Jun. 2, 2014, now Pat. No. 8,888,721, which is a continuation of application No. 13/213,930, filed on Aug. 19, 2011, now Pat. No. 8,771,206.

(51) Int. Cl.
  *A61B 5/00* (2006.01)
  *A61B 3/00* (2006.01)

(56) References Cited

U.S. PATENT DOCUMENTS

| | | | |
|---|---|---|---|
| 5,278,756 A | 1/1994 | Lemchen et al. | |
| 5,375,610 A * | 12/1994 | LaCourse | A61B 5/1104 33/512 |
| 5,524,637 A * | 6/1996 | Erickson | A61B 5/1038 482/8 |
| 5,791,351 A * | 8/1998 | Curchod | A61B 5/1121 600/587 |
| 6,072,494 A * | 6/2000 | Nguyen | G06F 3/017 345/156 |
| 6,176,837 B1 | 1/2001 | Foxlin | |
| 6,228,038 B1 * | 5/2001 | Claessens | A61B 3/113 351/210 |
| 6,409,687 B1 | 6/2002 | Foxlin | |
| 6,774,885 B1 * | 8/2004 | Even-Zohar | A61B 5/1036 345/156 |
| 7,231,834 B2 * | 6/2007 | Kurono | A61B 5/1038 348/61 |
| 7,315,249 B2 * | 1/2008 | Littell | A61B 5/103 340/573.1 |
| 7,395,181 B2 | 7/2008 | Foxlin | |
| 7,956,894 B2 * | 6/2011 | Akers | G06Q 50/22 348/207.1 |
| 7,988,647 B2 * | 8/2011 | Bunn | A61B 5/1038 600/587 |
| 8,075,449 B2 * | 12/2011 | Lee | A61B 5/1071 463/36 |
| 8,231,555 B2 | 7/2012 | Skelton et al. | |
| 8,269,826 B2 * | 9/2012 | Nieminen | A61B 5/1121 348/77 |
| 8,282,580 B2 | 10/2012 | Skelton et al. | |
| 8,292,832 B2 * | 10/2012 | Vallone | G06F 19/3481 128/920 |
| 8,323,218 B2 | 12/2012 | Davis et al. | |
| 8,469,901 B2 * | 6/2013 | Teicher | A61B 5/7282 600/595 |
| 8,556,831 B1 * | 10/2013 | Faber | A42B 3/046 340/500 |
| 8,579,834 B2 * | 11/2013 | Davis | A61B 5/0031 600/509 |
| 2003/0071118 A1 | 4/2003 | Gershman et al. | |
| 2003/0203730 A1 * | 10/2003 | Wan | G08B 13/19621 455/404.2 |
| 2003/0228033 A1 * | 12/2003 | Daniel | A61B 5/1038 382/104 |
| 2004/0059264 A1 * | 3/2004 | Nishibe | A61B 5/1038 600/587 |
| 2004/0228510 A1 * | 11/2004 | Berthonnaud | A61B 5/103 382/128 |
| 2005/0182341 A1 | 8/2005 | Katayama et al. | |
| 2005/0270163 A1 * | 12/2005 | Littell | A61B 5/103 340/573.7 |
| 2006/0094934 A1 | 5/2006 | Shirai et al. | |
| 2006/0200356 A1 | 9/2006 | Wan | |
| 2007/0027369 A1 * | 2/2007 | Pagnacco | A61B 5/1071 600/301 |
| 2007/0197938 A1 * | 8/2007 | Tyson | A61B 5/1072 600/587 |
| 2008/0021351 A1 * | 1/2008 | Teicher | A61B 5/1128 600/595 |
| 2008/0119763 A1 * | 5/2008 | Wiener | A61B 5/224 600/587 |
| 2008/0191864 A1 * | 8/2008 | Wolfson | G06F 3/011 340/524 |
| 2008/0221487 A1 * | 9/2008 | Zohar | A61B 5/103 600/595 |
| 2008/0228042 A1 * | 9/2008 | Schmidt | A61B 5/0002 600/300 |
| 2008/0287821 A1 | 11/2008 | Jung et al. | |
| 2008/0294013 A1 * | 11/2008 | Gobeyn | A61B 5/0059 600/300 |
| 2009/0030345 A1 | 1/2009 | Bonnet et al. | |
| 2009/0055223 A1 * | 2/2009 | Jung | G06F 19/322 705/3 |
| 2009/0082701 A1 * | 3/2009 | Zohar | A61B 5/103 600/595 |
| 2009/0099480 A1 | 4/2009 | Salgo et al. | |
| 2009/0163834 A1 * | 6/2009 | Wilssens | A61B 5/1036 600/592 |
| 2009/0177109 A1 * | 7/2009 | Yeh | A61B 5/103 600/546 |
| 2009/0227904 A1 * | 9/2009 | Mordaunt | G06K 9/00201 600/587 |
| 2009/0233769 A1 * | 9/2009 | Pryor | B60K 35/00 482/8 |
| 2009/0233770 A1 * | 9/2009 | Vincent | A63B 24/0021 482/8 |
| 2009/0240113 A1 * | 9/2009 | Heckerman | A61B 5/0002 600/300 |
| 2009/0287120 A1 | 11/2009 | Ferren et al. | |
| 2009/0306484 A1 * | 12/2009 | Kurtz | A61B 5/0059 600/300 |
| 2009/0315740 A1 * | 12/2009 | Hildreth | G06F 3/017 341/20 |
| 2010/0010383 A1 | 1/2010 | Skelton et al. | |
| 2010/0010389 A1 | 1/2010 | Davis et al. | |
| 2010/0010432 A1 | 1/2010 | Skelton | |
| 2010/0049095 A1 | 2/2010 | Bunn et al. | |
| 2010/0094174 A1 * | 4/2010 | Choi | A61B 5/1127 600/587 |
| 2010/0121228 A1 * | 5/2010 | Stirling | A61B 5/1127 600/595 |
| 2010/0174586 A1 | 7/2010 | Berg et al. | |
| 2010/0179438 A1 * | 7/2010 | Heneghan | A61B 5/0205 600/484 |
| 2010/0199228 A1 * | 8/2010 | Latta | G06F 3/011 715/863 |
| 2010/0204616 A1 | 8/2010 | Shears et al. | |
| 2010/0234769 A1 * | 9/2010 | Poliac | A61B 5/1038 600/592 |
| 2010/0312143 A1 * | 12/2010 | Kim | A61B 5/0064 600/587 |
| 2010/0312144 A1 * | 12/2010 | Connor | G06T 7/60 600/587 |
| 2011/0052005 A1 * | 3/2011 | Selner | A61B 5/1127 382/103 |
| 2011/0060248 A1 * | 3/2011 | Ishida | A61B 5/1113 600/587 |
| 2011/0066003 A1 * | 3/2011 | Duffy | A61B 5/16 600/300 |
| 2011/0066082 A1 * | 3/2011 | Duffy | A61B 5/1113 600/595 |
| 2011/0072457 A1 * | 3/2011 | Lanfermann | A63B 24/0006 725/34 |
| 2011/0077700 A1 | 3/2011 | Rofougaran | |
| 2011/0095916 A1 * | 4/2011 | Kass | A61B 5/0002 341/20 |
| 2011/0137144 A1 | 6/2011 | Rofougaran et al. | |
| 2011/0160550 A1 * | 6/2011 | Hwang | G06F 17/30032 600/301 |
| 2011/0172564 A1 | 7/2011 | Drew | |
| 2011/0245629 A1 * | 10/2011 | Giftakis | A61B 5/0476 600/301 |
| 2011/0246165 A1 | 10/2011 | Dai et al. | |

(56) References Cited

U.S. PATENT DOCUMENTS

| | | | |
|---|---|---|---|
| 2011/0263946 A1* | 10/2011 | el Kaliouby | A61B 5/1128 600/300 |
| 2011/0270132 A1* | 11/2011 | Mezghani | A61B 5/1038 600/587 |
| 2011/0295083 A1 | 12/2011 | Doelling et al. | |
| 2011/0313325 A1* | 12/2011 | Cuddihy | G08B 21/0476 600/595 |
| 2012/0022884 A1* | 1/2012 | Chillemi | A61B 5/1121 705/2 |
| 2012/0083714 A1 | 4/2012 | Yuen et al. | |
| 2012/0116252 A1 | 5/2012 | Newman et al. | |
| 2012/0143064 A1 | 6/2012 | Cyphery et al. | |
| 2012/0143093 A1 | 6/2012 | Stirling et al. | |
| 2012/0165703 A1* | 6/2012 | Bottum | G06F 19/3431 600/595 |
| 2012/0271143 A1* | 10/2012 | Aragones | G06F 19/3481 600/407 |
| 2012/0310117 A1* | 12/2012 | Teicher | A61B 5/1124 600/595 |
| 2013/0006151 A1* | 1/2013 | Main | A61B 5/103 600/587 |
| 2013/0035612 A1* | 2/2013 | Mason | A61B 5/1124 600/595 |
| 2013/0123666 A1 | 5/2013 | Giuffrida et al. | |

* cited by examiner

INTERACTIVE VIRTUAL CARE

PRIORITY

This application is a Continuation of commonly assigned and co-pending U.S. patent application Ser. No. 14/842,519, filed Sep. 1, 2015, and entitled "INTERACTIVE VIRTUAL CARE", which is a Continuation of commonly assigned and co-pending U.S. patent application Ser. No. 14/513,960, filed Oct. 14, 2014, issued as U.S. Pat. No. 9,149,209 on Oct. 6, 2015, and entitled "INTERACTIVE VIRTUAL CARE", which is a Continuation of commonly assigned U.S. patent application Ser. No. 14/293,562, filed Jun. 2, 2014, issued as U.S. Pat. No. 8,888,721 on Nov. 18, 2014, and entitled "INTERACTIVE VIRTUAL CARE", which is a Continuation of commonly assigned U.S. patent application Ser. No. 13/213,930, filed Aug. 19, 2011, issued as U.S. Pat. No. 8,771,206 on Jul. 8, 2014, and entitled "INTERACTIVE VIRTUAL CARE", which are incorporated by reference in their entireties.

BACKGROUND

In facilities, such as, for example, a health care facility, where an individual's movements may be evaluated, an individual (e.g., a patient) may be evaluated by a health care provider. The evaluation may be based, for example, on visual inspection of the individual's movements. Such visual inspection can result in subjective diagnosis based on the health care provider's interpretation of the individual's movements. The degree or type of impairment of an individual's movements can be a relevant factor in interpretation of the individual's movements. An objective understanding of an individual's movements may facilitate accurate interpretation.

BRIEF DESCRIPTION OF DRAWINGS

The embodiments are described with reference to the following figures.

DETAILED DESCRIPTION OF EMBODIMENTS

Figure 1:
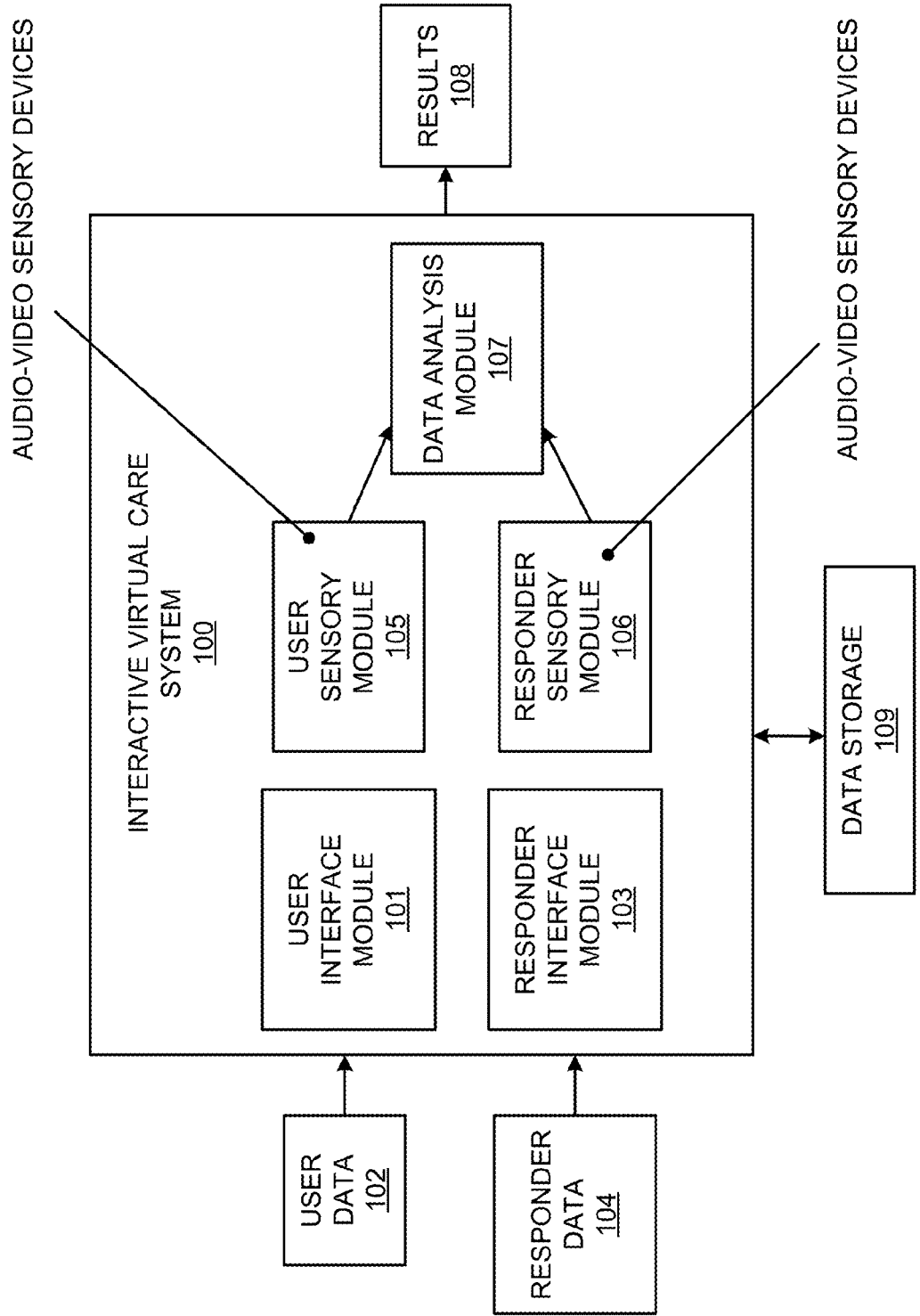
FIG. 1 illustrates a system diagram for an interactive virtual care system, according to an embodiment.

For simplicity and illustrative purposes, the principles of the embodiments are described by referring mainly to examples thereof. In the following description, numerous specific details are set forth in order to provide a thorough understanding of the embodiments. It will be apparent that the embodiments may be practiced without limitation to all the specific details. Also, the embodiments may be used together in various combinations.

An interactive virtual care system may provide for highly interactive virtual care consultations, for example, between two remote individuals. For facilities, such as, for example, a health care facility, the individuals may include a user (e.g., a patient) and a responder (e.g., a health care provider) located at a remote location from the user. The discussion below includes examples of application of the system for a patient and a health care provider. However, the system may be used with other industries for evaluation of any type of movement of an individual. For a health care facility, the system may provide for face-to-face video and two-way sharing of a patient's health information, and further include the use of computer-vision technology to assist the remote interaction by capturing and analyzing, for example, the patient's movements. These capabilities may offer a remote health care provider an enhanced view of a patient's condition. The system may also provide for computer-assisted speech and audio analysis of a health care provider's and patient's interactions.

The interactive virtual care system may include a user sensory module to acquire multi-modal user data related to user movement. The modules and other components of the system may include machine readable instructions, hardware or a combination of machine readable instructions and hardware. Multi-modal user data may refer to data acquired by multiple modes of input or output, such as a depth camera and/or a microphone array as discussed below. A data analysis module may compare the multi-modal user data to predetermined historical user data and/or statistical norm data for users to identify an anomaly in the user movement. The user sensory module may include a depth camera to acquire the multi-modal user data. The user sensory module may also include a microphone array to acquire multi-modal user data related to speech. A responder sensory module may acquire multi-modal responder data related to responder movement. The data analysis module may compare the multi-modal user data to the multi-modal responder data to identify an anomaly in the user movement. A user and/or responder interface modules may display a computer-generated version of the user movement that highlights movements of predetermined portions of a user's body. The user and/or responder interface modules may further display a real-time version of the user movement adjacent to and/or superimposed on the computer-generated version of the user movement, for example, to facilitate identification of an anomaly. The user and/or responder interface modules may further highlight the anomaly in the user movement in the computer-generated version of the user movement. For comparison of the multi-modal user data to the predetermined historical user data, a range of the predetermined historical user data may be selectable. The user and/or responder interface modules may include, for example, a keyboard and/or touch screen format for data entry.

A method for interactive virtual care may include acquiring multi-modal user data related to user movement, and comparing the multi-modal user data to predetermined historical user data and/or statistical norm data for users to identify at least one anomaly in the user movement. The method may further include acquiring the multi-modal user data by a depth camera and multi-modal user data related to speech by a microphone array. The method may include displaying a computer-generated version of the user movement that highlights movements of predetermined portions of a user's body. The method may include displaying a real-time version of the user movement adjacent to and/or superimposed on the computer-generated version of the user movement. The method may include highlighting the anomaly in the user movement in the computer-generated version of the user movement.

A non-transitory computer readable medium having stored thereon a computer executable program to provide interactive virtual care, the computer executable program when executed may cause a computer system to acquire multi-modal user data related to user movement, and compare the multi-modal user data to predetermined historical user data and/or statistical norm data for users to identify at least one anomaly in the user movement.

An example of a use scenario of the interactive virtual care system may include a user (e.g., a patient) with a medical condition visiting, for example, a retail clinic for a virtual visit with a remotely located responder (e.g., a health care provider). The user may be checked into the system by a nurse or another locally disposed health care provider. The health care provider may collect the user data, such as, for example, vitals and enter the information via the user interface module. The user data may be sent to the responder interface module for viewing by the remotely located responder. The remote responder may send, for example, exercises to the user interface module for user diagnosis and evaluation, and may otherwise communicate with the user via the responder sensory module. The user may perform the exercises or proceed as directed by the remote responder, and all user activities may be captured by the user sensory module. The data analysis module may analyze all data captured from the user and responder interface modules, and all data captured by the user and responder sensory modules to generate results based on comparison of user specific history data and/or history data of a range of users generally to determine any anomalies. The history data for the range of users may be in the form of statistical norms for users. These anomalies and other result data may be reported to the remote responder, whereby the responder may diagnose the user's condition and render appropriate treatment in the form of a prescription or other activities.

As discussed above, the interactive virtual care system may provide remote acquisition of multi-modal user data via the user sensory module, which may include, for example, high-fidelity audio-video sensory devices. Likewise, responder data may be remotely acquired via the responder sensory module, which may also include, for example, high-fidelity audio-video sensory devices. As described in detail below, the audio-video sensory devices may include, for example, a depth camera and microphone arrays. The depth camera may include, for example, a MICROSOFT KINECT camera system. In a healthcare environment, the data acquired from the user and responder sensory modules may be used to augment patient reported symptoms and professionally obtained biometric data to assist a remote health care provider in arriving at more accurate medical diagnoses.

As discussed herein, the interactive virtual care system may facilitate an interactive care delivery approach that may involve the use of user data to help a responder arrive at more accurate medical diagnoses. For example, data related to a user's walking and gesture patterns (e.g., gaits, strides, balances) may be acquired unobtrusively using, for example, depth-perceiving camera arrays. Data related to a user's vocal and/or speech patterns may be acquired unobtrusively using, for example, microphone arrays. The visual and audio data may be transmitted to the data analysis module and analyzed for anomaly identification by comparing, for example, population norms as well as historical patterns of the particular user. Such anomalies may be highlighted and presented on the user and/or responder interface modules based on the system configuration. For example, the responder interface module may be used by a health care provider at a remote location to simultaneously view a real-time live video stream of the user (e.g., the patient) performing an action (e.g., walking, stretching) side-by-side with results generated by the data analysis module to assist in arriving at a medical diagnosis. The results generated by the data analysis module may also be shown as an overlay to the real-time video stream of the user.

The interactive virtual care system may also be used in an unsupervised environment (e.g., without interaction with a responder) to provide a user (e.g., a patient) visual cues to guide the user through the correct process. For example, a treatment process (e.g., physical therapy routine or exercise) may be observed, validated and recorded under the direction of a health care provider at a remote location. A derivative outline from the recorded footage may be used to automatically guide a user through a treatment process regimen while the user is in an unsupervised setting, such as, for example, at home. The user's subsequent unsupervised in-home exercise/physical therapy sessions may be recorded and transmitted through the same remote hosting application for purposes of being viewed by a remote health care provider and/or additional analysis and comparison against the user's historical patterns. As the remote health care provider monitors the user's progress, the remote health care provider may adapt the user's treatment regimen over time, for example, by adjusting and transmitting a new or modified derivative outline from the user's recorded footage.

The interactive virtual care system may be usable, for example, to provide remote health care expertise to any environment located a distance away from a primary health care provider, such as, for example, a remote clinic. The system may also be usable at any location convenient to a user, such as, for example, a user's home. The system may be usable in a stand-alone configuration, such as, for example, a kiosk, or may be uploaded to an existing computer system, for example, in a clinic environment.

The systems and methods described herein provide a technical solution to the technical problem of comparing user movement and/or speech with prior historical data or statistical norms for users to determine anomalies. In many instances, manual comparison of user movement or speech with prior historical data or statistical norms is not a viable solution given the size of such data and variability involved in the manual comparison, which can lead to inconsistent results. The systems and methods according to the embodiments provide the technical solution of objectively determining anomalies based on, for example, a computer-generated version of the user movement that highlights anomalies.

FIG. 1 illustrates an interactive virtual care system 100, according to an embodiment. Referring to FIG. 1, the system 100 may include a user interface module 101 to input user data 102, and a responder interface module 103 to input responder data 104. As described in further detail below, the various components of the system 100 may be operable to capture and analyze data from multiple users and responders, which may include data pertaining to a user, for example a patient, and data pertaining to a responder, for example a health care provider. The modules and sub-components of the system 100 may be combined or partitioned without departing from the scope of the system 100, and are partitioned as shown in FIG. 1 for facilitating an understanding of the system 100. For example, the user and responder interface modules 101, 103 may be combined as a general system interface module. A user sensory module 105 may include audio and video capture and relay capabilities for respectively capturing and relaying information related to a user to a responder. A responder sensory module 106 may likewise include audio and video capture and relay capabilities for respectively capturing and relaying information from a responder to a user. A data analysis module 107 may analyze the user and responder data 102, 104 and data captured by the user and responder sensory modules 105, 106 to generate results 108, such as, for example, patient specific metrics to a health care provider or results and/or instructions to a patient. The data analysis module 107 may be implemented in a cloud environment, instead of as a component of the system 100. The system 100 may provide for the same data to be viewed by either the user or the responder without sending the actual data between the user and responder interface modules 101, 103. A data storage 109 may be provided for storing information utilized by the system 100, which may include, for example, user specific history data or history data of a range of users generally. The user data and history data may be used to generate statistical norms used for comparison as described below.

Figure 2:
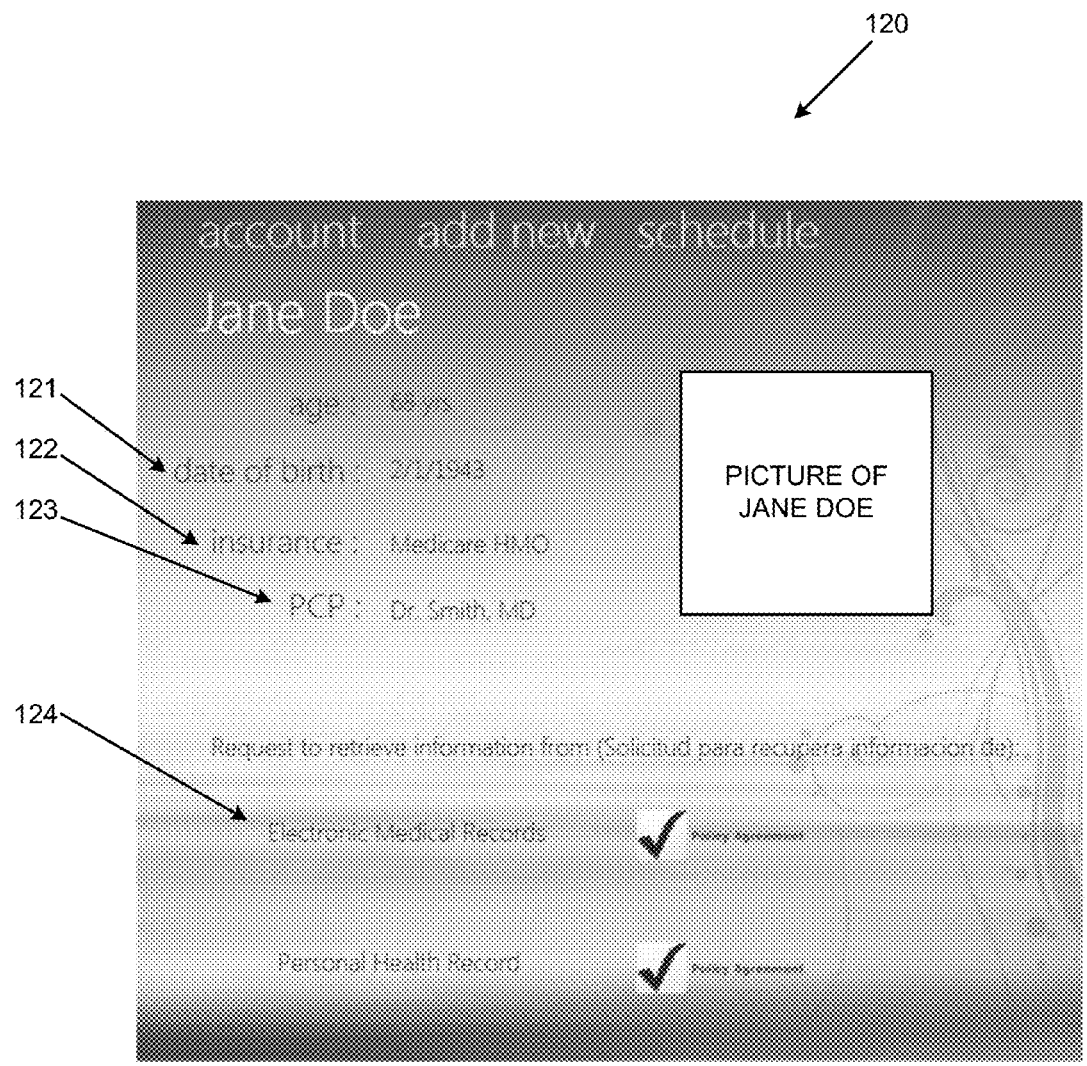
FIG. 2 illustrates an example of a screen display for the interactive virtual care system, illustrating, for example, a user view of general user data.

Referring to FIG. 2, an example is shown of a user screen display 120 for the user interface module 101, illustrating, for example, use of the system 100 in a health care facility and a patient view of general patient data. The screen display 120 may include, for example, general patient data, such as, patient date of birth at 121, insurance information at 122, health care provider information at 123, and agreements to proceed with the virtual health care process at 124.

Figure 3:
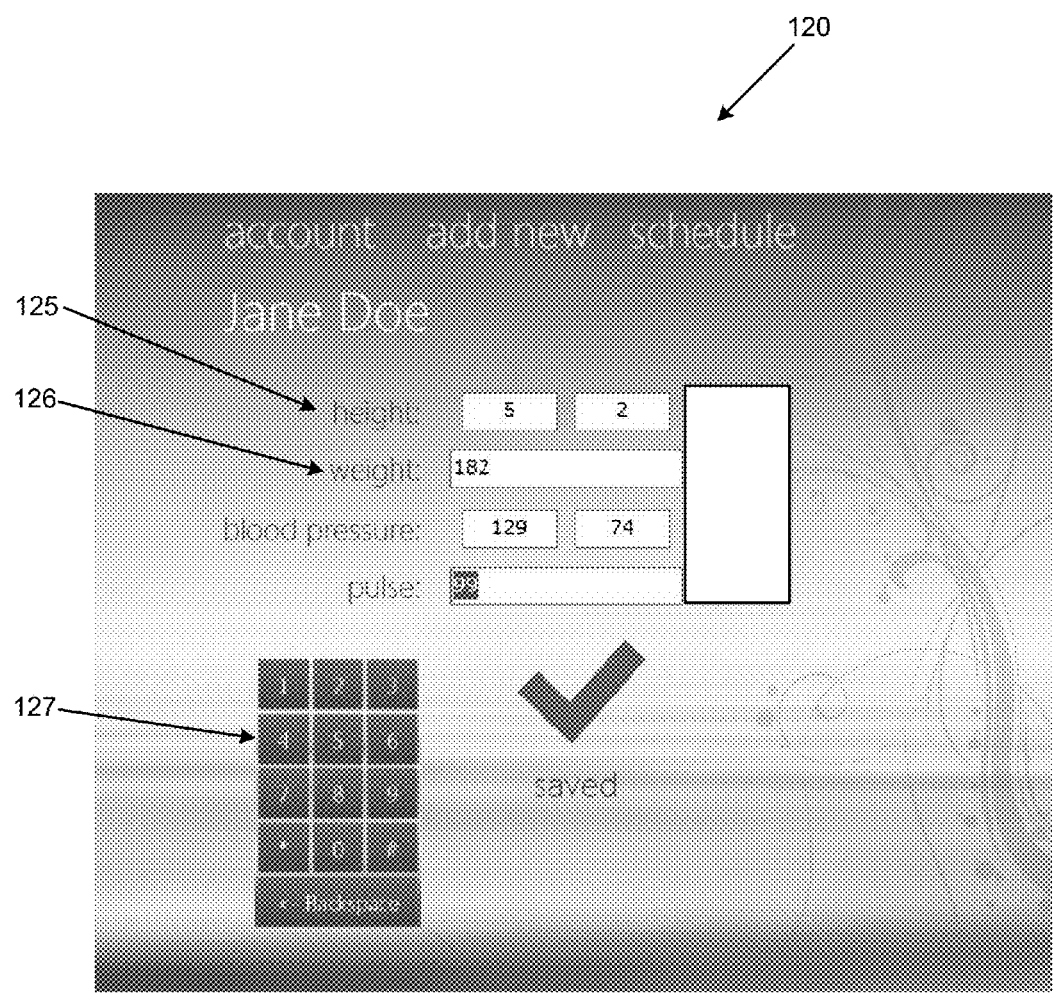
FIG. 3 illustrates an example of a screen display for the interactive virtual care system, illustrating, for example, user vital data entry.

FIG. 3 illustrates an example of the user screen display 120 illustrating, for example, patient vital data entry. The screen display 120 may include, for example, patient vital data, such as, patient height at 125, weight at 126 etc., and a touch screen keypad 127 for entry of the patient vital data. Alternatively, biometric devices, such as, for example, a blood pressure monitor or a weight scale may be coupled to the user sensory module 105 for automatic capture of patient vital data.

Figure 4:
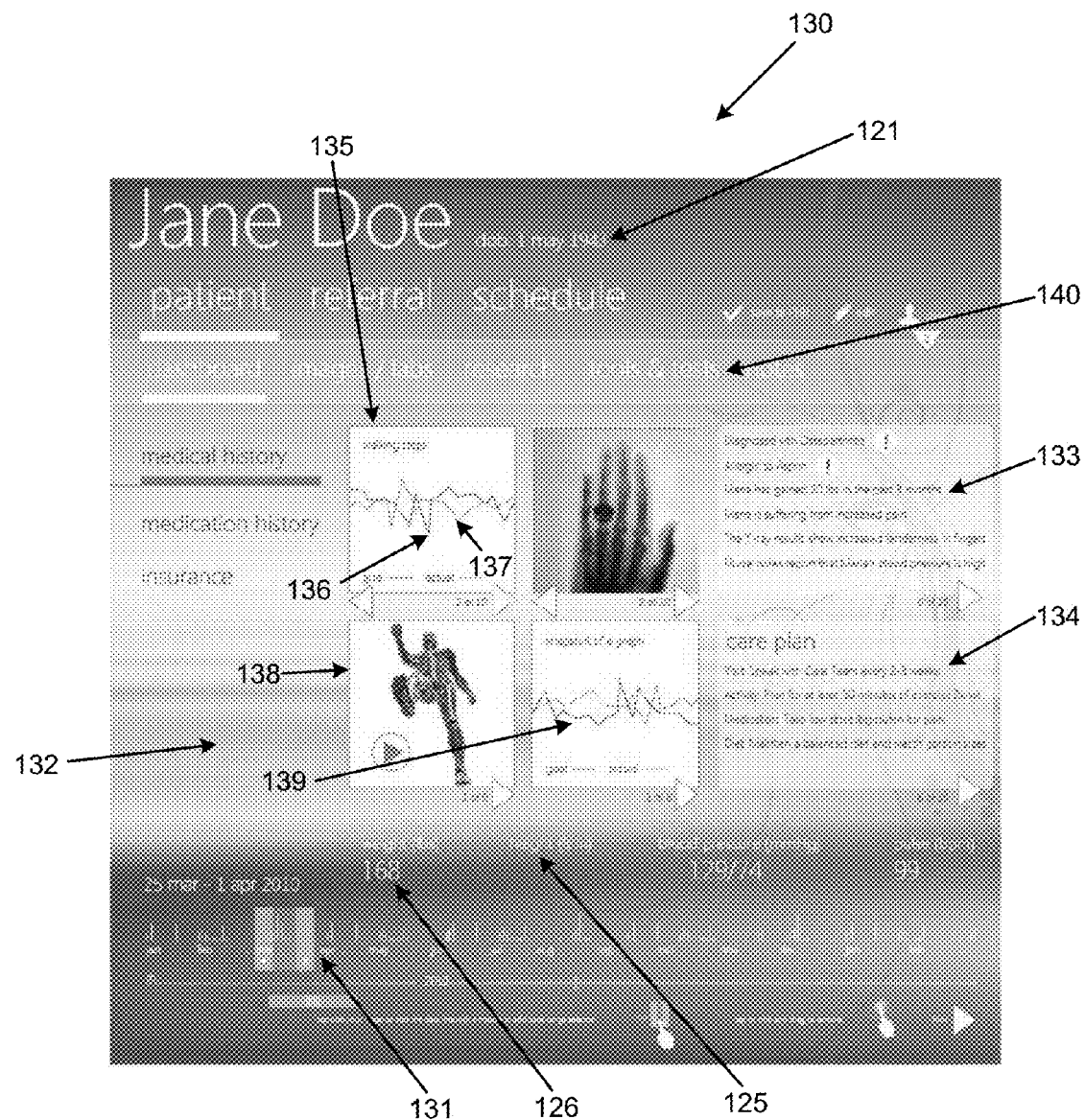
FIG. 4 illustrates an example of a screen display for the interactive virtual care system, illustrating, for example, a responder view of general and user vital data.

Referring to FIG. 4, an example is shown of a responder screen display 130 for the responder interface module 103, illustrating, for example, a health care provider view of the general and patient vital data. For the system 100 implemented, for example, as a kiosk, the screen displays 120, 130 may be provided adjacent each other so that the user and healthcare provider may each see two or more displays. As discussed above, the screen displays 120, 130 are provided for illustrative purposes only and may be combined in a single or distributed across other multiple displays. For example, a user may see the screen display 120 including user specific information and the screen display 130 including instructions from the responder as a combined display.

Referring to FIG. 4, the screen display 130 may include, for example, general patient data, such as, patient date of birth at 121, and patient vital data, such as, patient height at 125, weight at 126 etc. The screen display 130 may also include a timeline 131 selectable to determine a patient's medical history for comparison. For example, as shown in FIG. 4, a health care provider may select a timeline from Mar. 25, 2010-Apr. 1, 2010. The user medical records may be displayed at windows 132, and may include, for example, notes related to previous patient ailments at 133 and health care provider diagnosis at 134. Other windows may display metrics related to a patient's walking goals at 135, with the goal metrics being displayed at 136 and patient actual metrics being displayed at 137. A history of patient performance in other tests may be displayed at 138 and 139.

Figure 5:
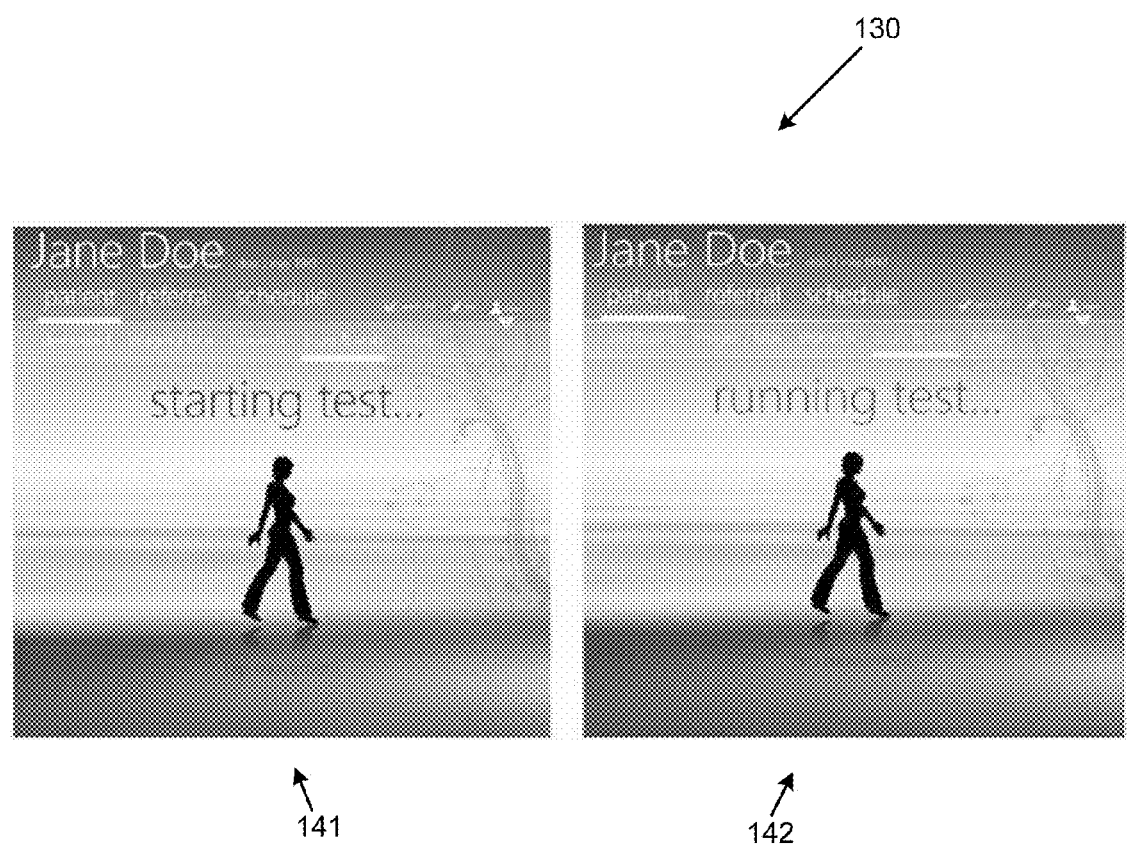
FIG. 5 illustrates an example of a screen display for the interactive virtual care system, illustrating, for example, a responder view of a user movement test.
Figure 6:
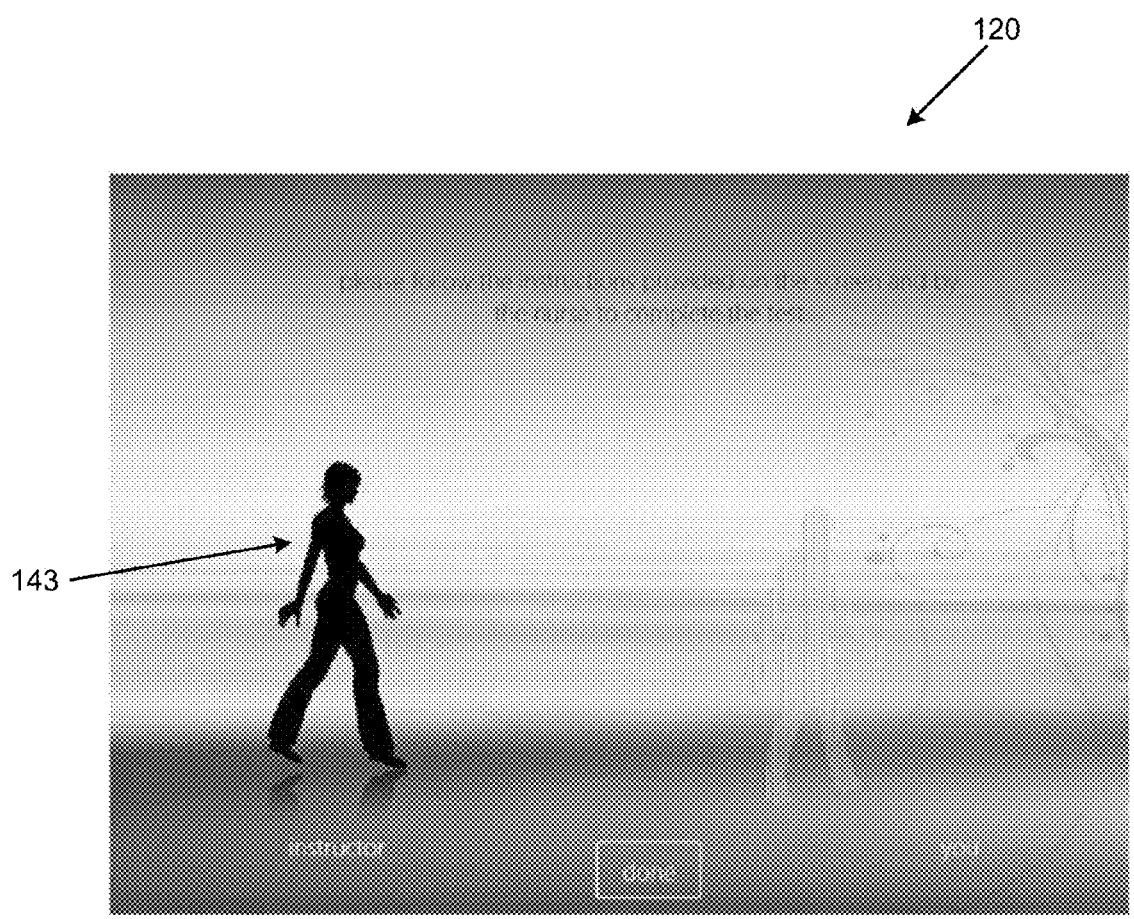
FIG. 6 illustrates an example of a screen display for the interactive virtual care system, illustrating, for example, a user view of remote movement instructions.

FIG. 5 illustrates an example of the screen display 130, illustrating, for example, a health care provider view of a patient movement test which may be initiated by selecting a "tools & tests" option at 140 as shown in the FIG. 4 screen display. Assuming for example the user complains of knee pain, the test options 141 or 142 may be selected. FIG. 6 illustrates an example of the user screen display 120, illustrating, for example, a patient view of remote movement instructions. Assuming the health care provider selects the test at 141, the user screen display 120 may provide the patient an example of movement at 143 requested by the health care provider. For example, the patient may be requested to walk ten feet as shown in the illustration of FIG. 6.

Figure 7:
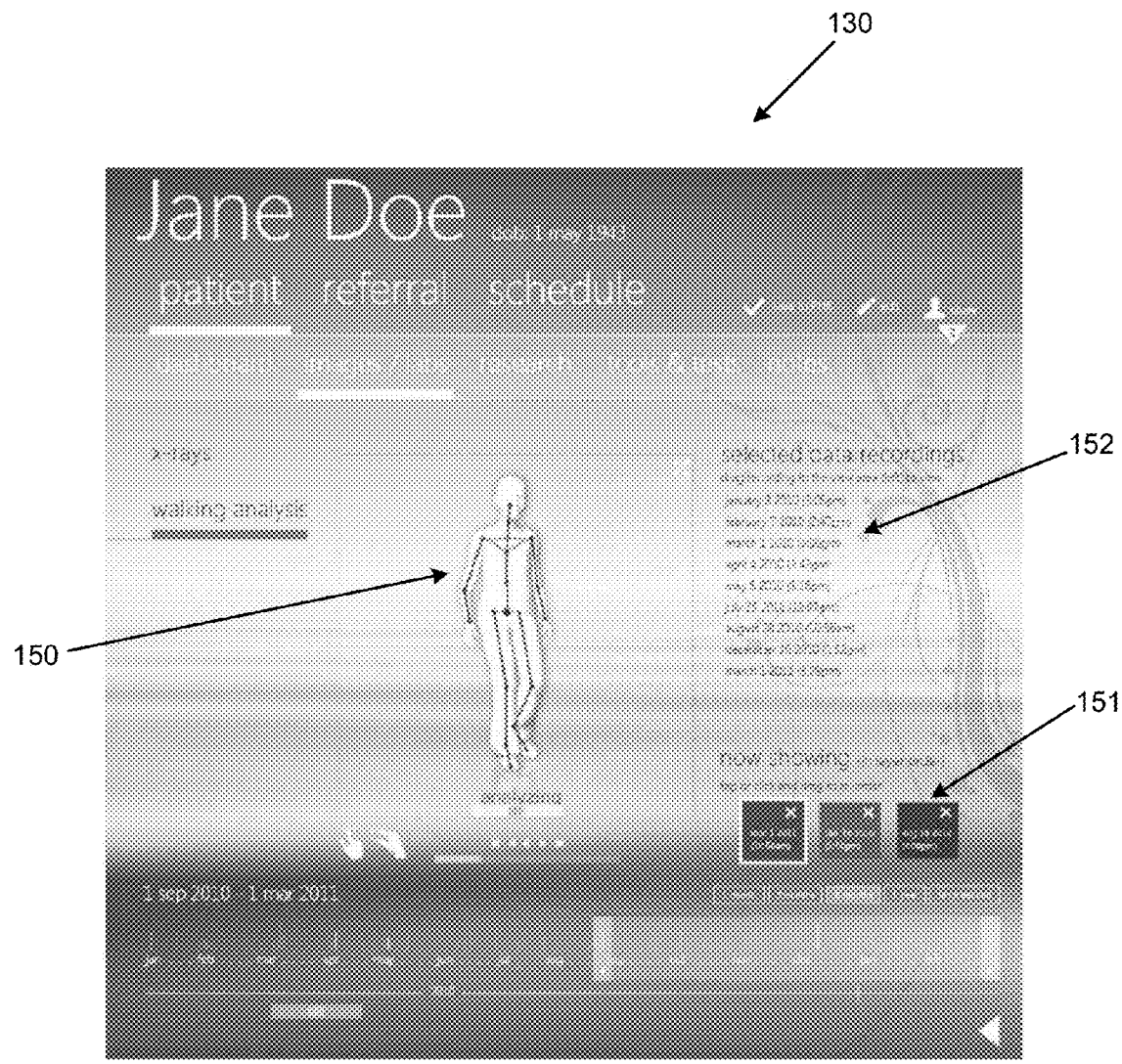
FIG. 7 illustrates an example of a screen display for the interactive virtual care system, illustrating, for example, a responder view of user movement.

Referring to FIG. 7, an example of the responder screen display 130 may illustrate, for example, a health care provider view of patient movement recorded by the user sensory module 105. The user sensory module 105 may include high-fidelity audio-video sensory devices. The audio-video sensory devices may include, for example, a depth camera and microphone arrays. The depth camera may include, for example, a MICROSOFT KINECT camera system. Responder data may also be acquired via the responder sensory module 106, which may also include, for example, high-fidelity audio-video sensory devices. The user sensory module 105 may provide real-time digitization of user movement to produce a computer-generated version of the user movement that highlights anomalies, where the movement may be displayed at 150. For example, an anomaly related to a knee joint may highlight the knee joint area in the display at 150 and/or provide metrics related to the degree or extent of the anomaly in the results 108. The real-time digitization may be based on interpretation of movement by the user sensory module 105.

Options for selecting user historical movements may be presented at 151, and a listing of all previously recorded user movement analysis may be presented at 152. The data acquired from the user sensory module 105 may be used to augment patient reported symptoms and the biometric data related to patient movement at 150 to assist the remote health care provider in arriving at more accurate medical diagnoses. Data related to the user's vocal and/or speech patterns may also be acquired by the user sensory module 105 by using, for example, microphone arrays.

Figure 8:
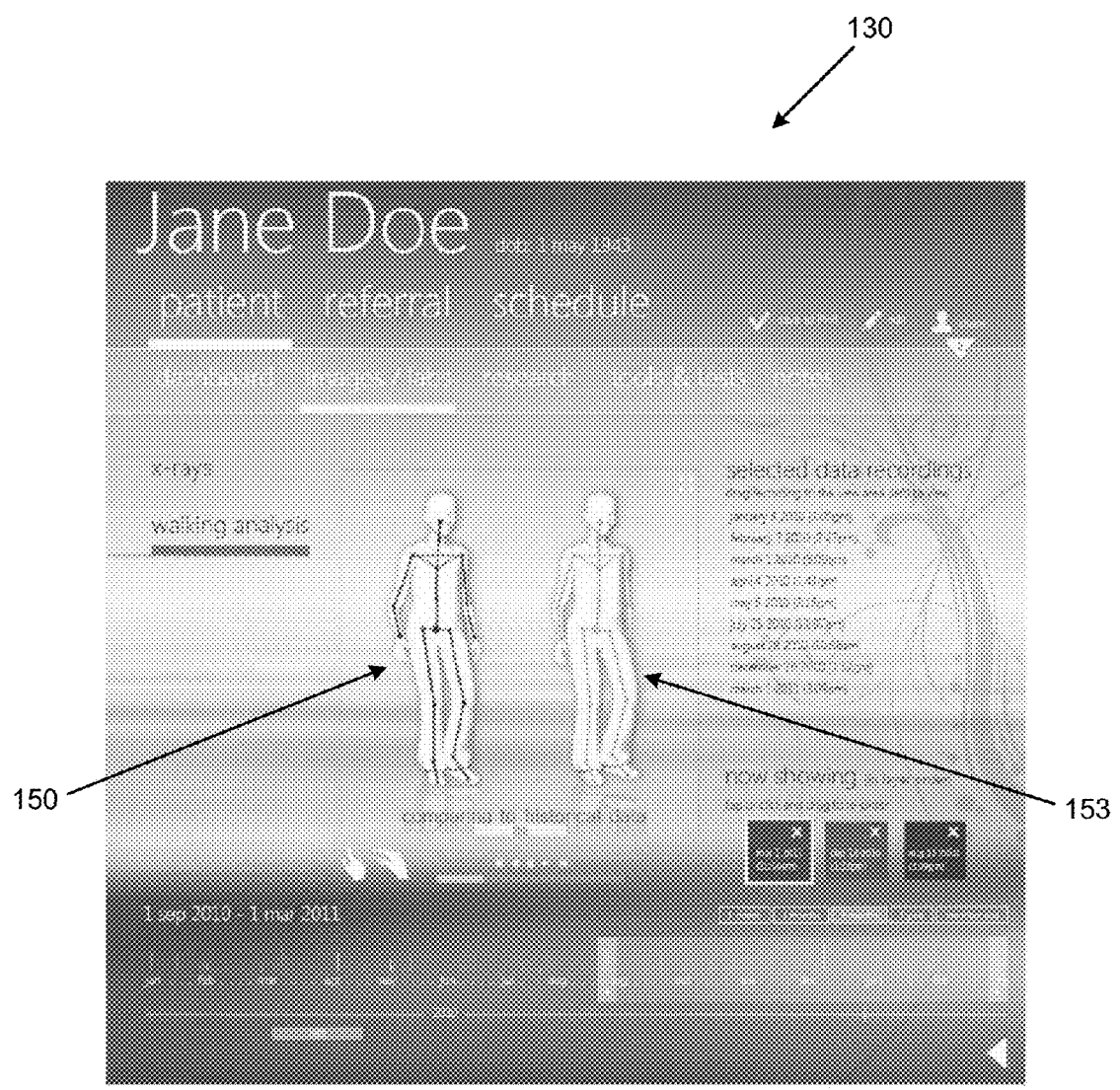
FIG. 8 illustrates an example of a screen display for the interactive virtual care system, illustrating, for example, a responder view of user movement and historical analysis.

Referring to FIG. 8, an example is shown of the screen display 130, illustrating, for example, a health care provider view of patient movement and historical analysis. Referring to FIGS. 7 and 8, assuming a comparison is made between a patient's current movement at 150 and historical movement at 153, the current and historical movements may be displayed adjacent each other as shown. The historical movement may be selected from the user historical movements at 151 or the listing of previously recorded user analysis at 152. Based on the selection, the data analysis module 107 may perform an analysis for anomaly identification by comparing the patient's current movement at 150 with the patient's selected historical movement. Alternatively, the data analysis module 107 may perform an analysis for anomaly identification by comparing the patient's current movement at 150 with statistical population norms, and identifying any significant deviation from such population norms. Such anomalies may be highlighted and presented on the user and/or responder interface modules 101, 103 based on the system configuration. For example, the responder interface module 103 may include the display at 130 as shown in FIG. 8. The display may be used by a health care provider at a remote location to simultaneously view in real-time a live video stream of the user (e.g., the patient) performing an action side-by-side with the computer-generated results (e.g., the patient's current movement at 150) generated by the data analysis module 107 to assist in arriving at a medical diagnosis. Based on anomaly identification, the health care provider at the remote location may provide a medical diagnosis and further instructions as needed.

The anomaly identification performed by the data analysis module 107 may be determined by comparing user specific movement and/or audio information with prior history information for the user (e.g., movement data collected 6 months ago), or with statistical norms of similar users. The similarity of users may be based, for example, on metrics such as age, gender, race, height, weight, general demographics and other health conditions. The real-time digitization of user movement captured by the user sensory module 105 may be used to compare points of interest for the patient to prior patient history information and/or statistical norms of similar users as described above. For example, for movement information, the data analysis module 107 may compare changes at various joints of a patient to determine, for example, limp development, changes in posture, a length of time taken for a certain movement etc. For example, in order to determine limp development, the data analysis module 107 may determine that based on a starting position, the patient has a longer stride using a right leg as compared to a left leg. Factors such as a length of time taken for certain movement may also be compared to historical data for the patient which may be used as a threshold to determine if there has been improvement compared to the historical data. Alternatively, factors such as a length of time taken for certain movement may also be compared to statistical norms which may be used as a threshold to determine if the user falls within or outside of such statistical norms.

The data analysis module 107 may also be trainable to recommend diagnosis based on anomaly identification. For example, for an anomaly related to a length of time it takes for movement of a right leg versus a left leg, or based on the length of a stride using a right leg versus a left leg, the data analysis module 107 may recommend a diagnosis related to limp development (e.g., physical therapy focused on gait). The data analysis module 107 may also be trainable to generate a recommended treatment based on the recommended diagnosis.

Figure 9:
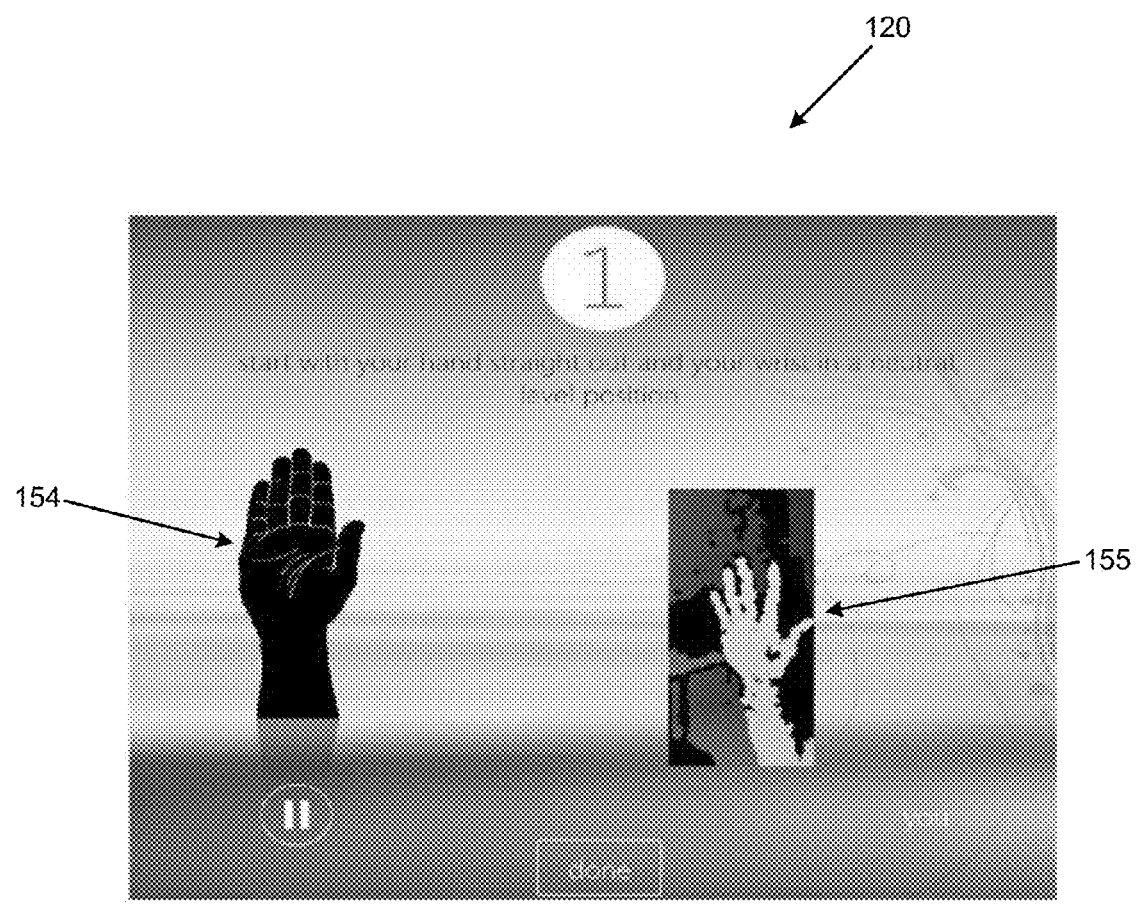
FIG. 9 illustrates an example of a screen display for the interactive virtual care system, illustrating, for example, a user view for on-screen instructions.

Referring to FIG. 9, an example is shown of the screen display 120, illustrating, for example, a user view for on-screen instructions. As shown in FIG. 9, an example of the on-screen instructions is shown at 154 where the user (e.g., the patient) may follow the instructions and the user's movements may be displayed in the window at 155. The on-screen instructions 154 of FIG. 9 may be performed with a responder (e.g., the health care provider) viewing the user response at a remote location or under unsupervised conditions. Alternatively, a user or a responder may record the on-screen instructions 154, which may serve as a template for the user to follow, and the user may perform the movements under unsupervised conditions. The template may serve as the baseline for anomaly identification. The data analysis module 107 may identify anomalies based on comparison of the data obtained by the user sensory module 105 with the template, or based on comparison of the data obtained by the user sensory module 105 with prior user-specific historical data or with statistical norms of similar users as discussed above. The user may also follow instructions from a responder and the multi-modal user data may be compared to the multi-modal responder data to identify an anomaly in the user movement. The identified anomalies may be subsequently analyzed by a responder (e.g., the health care provider).

Figure 10:
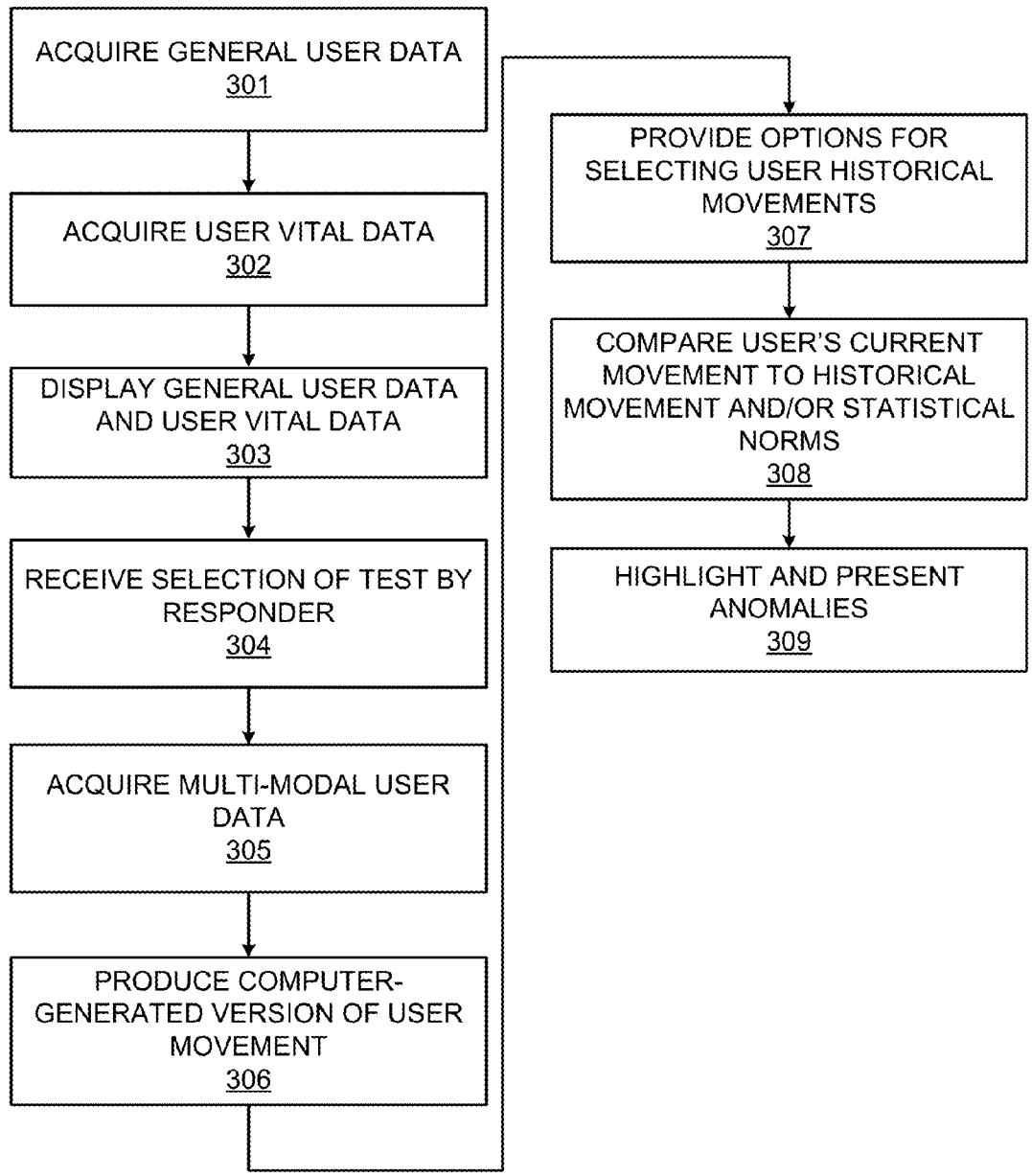
FIG. 10 illustrates a method for interactive virtual care, according to an embodiment.
Figure 11:
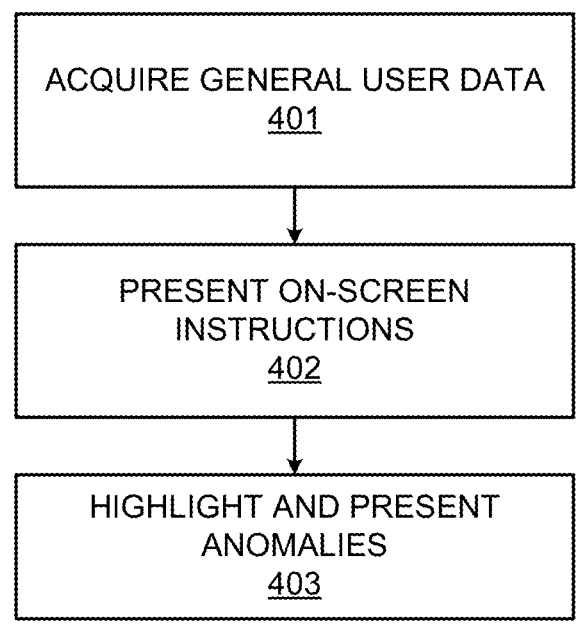
FIG. 11 illustrates a method for interactive virtual care, according to an embodiment.

FIG. 10 illustrates a flowchart of a method 300 for interactive virtual care, according to an embodiment. FIG. 11 illustrates a flowchart of a method 400 for interactive virtual care, according to an embodiment. The methods 300 and 400 may be implemented on the interactive virtual care system 100 described above with reference to FIGS. 1-9 by way of example and not limitation. The methods 300 and 400 may be practiced in other systems.

For the method 300, referring to FIGS. 1, 2 and 10, at block 301, for use in a health care facility, the interactive virtual care system 100 may acquire general user (e.g., patient) data, such as, patient date of birth at 121, insurance information at 122, health care provider information at 123, and agreements to proceed with the virtual health care process at 124. Capture of the general user data may be automated, for example, by attaching a magnetic strip card or a user-specific ID issued, for example, by a health insurer.

At block 302, referring to FIGS. 1, 3 and 10, the system 100 may acquire user vital data, such as, patient height at 125, weight at 126 etc.

At block 303, referring to FIGS. 1, 4 and 10, the system 100 may display the general user data and user vital data at the responder interface module 103. The system 100 may receive selection of the timeline 131, which is selectable to determine a patient's medical history for comparison. As discussed above, the user medical records may be displayed at windows 132, and may include, for example, notes related to previous patient ailments at 133 and health care provider diagnosis at 134. Other windows may display metrics related to a patient's walking goals at 135, with the goal metrics being displayed at 136 and patient actual metrics being displayed at 137. A history of patient performance in other tests may be displayed at 138 and 139.

At block 304, referring to FIGS. 1, 5 and 10, the system 100 may receive a selection of a test by a responder. For example, the system 100 may receive selection of the "tools & tests" option at 140 as shown in the FIG. 4 screen display. Assuming the system 100 receives selection of the test 141, the user screen display 120 may provide the patient an example of movement at 143 requested by the health care provider. For example, the patient may be requested to walk ten feet as shown in the illustration of FIG. 6.

At block 305, referring to FIGS. 1, 7 and 10, the user sensory module 105 may acquire multi-modal user data 102 related to user movement. Referring to FIG. 7, an example of the responder screen display 130 may illustrate, for example, a health care provider view of patient movement recorded by the user sensory module 105.

At block 306, referring to FIGS. 7 and 10, the user sensory module 105 may provide real-time digitization of user movement to produce a computer-generated version of the user movement that highlights anomalies, where the movement may be displayed at 150. The real-time digitization may be based on interpretation of movement by the user sensory module 105.

At block 307, referring to FIGS. 7 and 10, the responder interface module 103 may provide options for selecting user historical movements at 151, and a listing of all previously recorded user movement analysis may be displayed at 152.

At block 308, referring to FIGS. 1, 7, 8 and 10, the data analysis module 107 may compare a patient's current movement at 150 and historical movement at 153, with the current and historical movements being displayed adjacent each other as shown. The historical movement may be selected from the user historical movements at 151 or the listing of previously recorded user analysis at 152. Based on the selection, the data analysis module 107 may perform an analysis for anomaly identification by comparing the patient's current movement at 150 with the patient's selected historical movement. Alternatively, the data analysis module 107 may perform an analysis for anomaly identification by comparing the patient's current movement at 150 with statistical population norms, and identifying any significant deviation from such population norms.

At block 309, referring to FIGS. 1, 7, 8 and 10, the data analysis module 107 may highlight and present anomalies on the user and/or responder interface modules 101, 103 based on the system configuration. The data analysis module 107 may also generate metrics of the degree or extent of the anomalies as the results 108. For example, the responder interface module 103 may include the display at 130 as shown in FIG. 8. The display may be used by a health care provider at a remote location to simultaneously view in real-time a live video stream of the user (e.g., the patient) performing an action side-by-side with the computer-generated results (e.g., the patient's current movement at 150) generated by the data analysis module 107 to assist in arriving at a medical diagnosis. Based on anomaly identification, the health care provider at the remote location may provide a medical diagnosis and further instructions as needed.

For the method 400, referring to FIGS. 1, 9 and 11, at block 401, the interactive virtual care system 100 may acquire general user (e.g., patient) data.

At block 402, if a user is to perform tests under unsupervised conditions or following a responder's movements, the user interface module 101 may present on-screen instructions as shown at 154 where the user (e.g., the patient) may follow the instructions and the user's movements may be displayed in the window at 155. The on-screen instructions 154 of FIG. 9 may be performed with a responder (e.g., the health care provider) viewing the user response at a remote location or under unsupervised conditions. Alternatively, a user or a responder may record the on-screen instructions 154, which may serve as a template for the user to follow, and the user may perform the movements under unsupervised conditions. The template may serve as the baseline for anomaly identification. In the unsupervised setting, a user may contact the responder at a remote location for assistance as needed.

At block 403, the data analysis module 107 may identify anomalies based on comparison of the data obtained by the user sensory module 105 with the template, or based on comparison of the data obtained by the user sensory module 105 with prior user-specific historical data or with statistical norms of similar users as discussed above. The identified anomalies may be subsequently analyzed by a responder (e.g., the health care provider).

Figure 12:
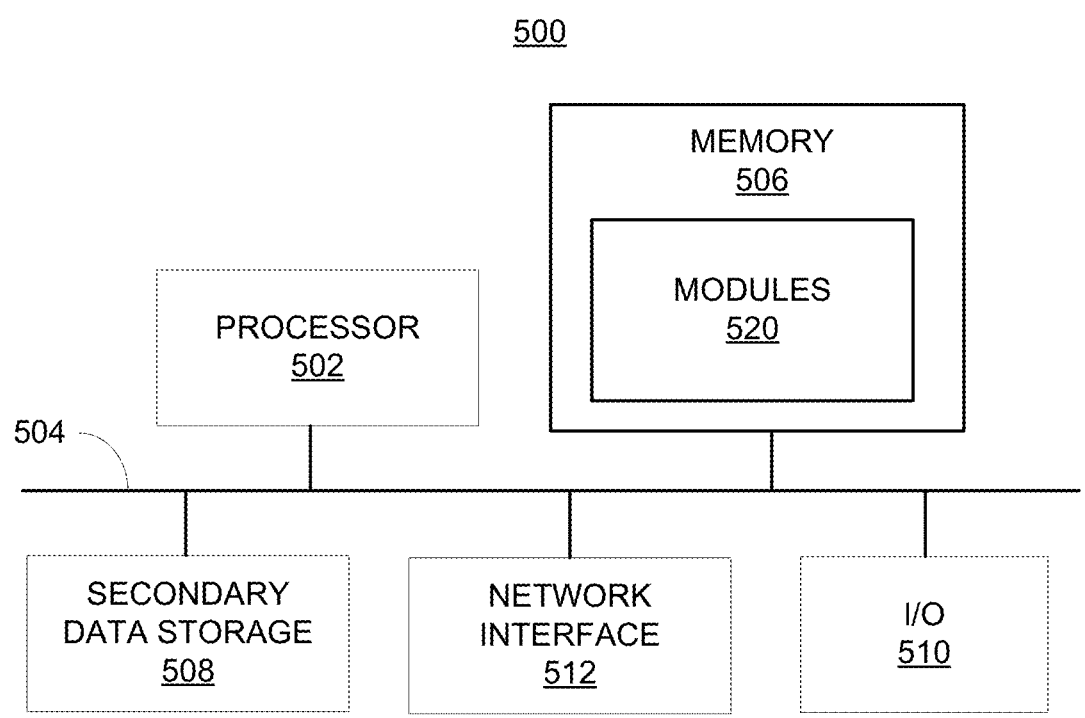
FIG. 12 illustrates a computer system, according to an embodiment.

FIG. 12 shows a computer system 500 that may be used with the embodiments described herein. The computer system 500 represents a generic platform that includes components that may be in a server or another computer system. The computer system 500 may be used as a platform for the system 100. The computer system 500 may execute, by a processor or other hardware processing circuit, the methods, functions and other processes described herein. These methods, functions and other processes may be embodied as machine readable instructions stored on computer readable medium, which may be non-transitory, such as hardware storage devices (e.g., RAM (random access memory), ROM (read only memory), EPROM (erasable, programmable ROM), EEPROM (electrically erasable, programmable ROM), hard drives, and flash memory).

The computer system 500 includes a processor 502 that may implement or execute machine readable instructions performing some or all of the methods, functions and other processes described herein. Commands and data from the processor 502 are communicated over a communication bus 504. The computer system 500 also includes a main memory 506, such as a random access memory (RAM), where the machine readable instructions and data for the processor 502 may reside during runtime, and a secondary data storage 508, which may be non-volatile and stores machine readable instructions and data. The memory and data storage are examples of computer readable mediums. The memory 506 may include modules 520 including machine readable instructions residing in the memory 506 during runtime and executed by the processor 502. The modules 520 may include the modules 101, 103 and 105-107 of the system 100 shown in FIG. 1.

The computer system 500 may include an I/O device 510, such as a keyboard, a mouse, a display, touchscreen, etc. The computer system 500 may include a network interface 512 for connecting to a network. Other known electronic components may be added or substituted in the computer system 500.

While the embodiments have been described with reference to examples, various modifications to the described embodiments may be made without departing from the scope of the claimed embodiments.

What is claimed is:

1. An interactive virtual care system comprising:
   at least one processor;
   and a memory storing machine readable instructions that when executed by the at least one processor cause the at least one processor to acquire, by at least one sensory device, user data related to user movement of at least one portion of a user's body, the user movement of the at least one portion of the user's body being performed at a distance away from the at least one sensory device;
   digitize, in real-time, the user movement of the at least one portion of the user's body based on an interpretation of the acquired user data;
   produce a computer-generated version of the user movement of the at least one portion of the user's body;
   transmit a signal of the digitized user movement of the at least one portion of the user's body based on the interpretation of the acquired user data and the computer-generated version of the user movement of the at least one portion of the user's body, wherein the signal is to provide for a display of the digitized user movement of the at least one portion of the user's body, and highlighting of the digitized user movement of the at least one portion of the user's body in the display of the digitized user movement of the at least one portion of the user's body, wherein the computer-generated version of the user movement of the at least one portion of the user's body includes joints of the user's body displayed as connectors and/or skeletal features of the user's body displayed as line segments between the connectors;

compare the acquired user data to predetermined historical user data and/or statistical norm data for other users to identify at least one anomaly in the user movement of the at least one portion of the user's body; and display the computer-generated version of the user movement of the at least one portion of the user's body, highlighting the at least one anomaly in the user movement of the at least one portion of the user's body identified to provide interactive virtual care.

2. The system of claim 1, wherein the at least one sensory device comprises a video sensor to acquire a video stream of the user movement of the at least one portion of the user's body.

3. The system of claim 1, wherein the at least one sensory device comprises an audio sensor to acquire user data related to speech.

4. The system of claim 1, wherein the machine readable instructions when executed by the at least one processor further cause the at least one processor to:

display a real-time version of the user movement of the at least one portion of the user's body adjacent to and/or superimposed on the computer-generated version of the user movement of the at least one portion of the user's body.

5. The system of claim 1, wherein the machine readable instructions when executed by the at least one processor further cause the at least one processor to:

display the computer-generated version of the user movement of the at least one portion of the user's body; and additionally display a real-time version of the user movement adjacent to and/or superimposed on the computer-generated version of the user movement of the at least one portion of the user's body.

6. The system of claim 1, wherein the machine readable instructions when executed by the at least one processor further cause the at least one processor to:

display the computer-generated version of the user movement of the at least one portion of the user's body; and highlight the at least one anomaly in the user movement of the at least one portion of the user's body identified in the computer-generated version of the user movement of the at least one portion of the user's body.

7. The system of claim 1, wherein the user movement of the at least one portion of the user's body includes walking, and the at least one portion of the user's body comprises one or both of the user's legs.

8. The system of claim 1, wherein the highlights of the digitized user movement of the at least one portion of the user's body include a computer-generated display of at least one internal feature of the at least one portion of the user's body.

9. The system of claim 1, wherein the predetermined historical user data and the statistical norm data for the other users respectively include computer-generated versions of movements of the at least one portion of the user's body and movements of the same at least one portion of bodies of the other users.

10. A method for interactive virtual care, the method comprising:

acquiring, by at least one processor, user data related to user movement of at least one portion of a user's body by using a user sensory module comprising at least one sensory device, the user movement of the at least one portion of the user's body being performed at a distance away from the user sensory module;

digitizing, by the at least one processor, the user movement of the at least one portion of the user's body based on an interpretation of the acquired user data by the user sensory module;

producing, by the at least one processor, a computer-generated version of the user movement of the at least one portion of the user's body;

generating, by the at least one processor, a signal of the digitized user movement of the at least one portion of the user's body based on the interpretation of the acquired user data by the user sensory module and the computer-generated version of the user movement of the at least one portion of the user's body, wherein the signal is to provide for a display of the digitized user movement of the at least one portion of the user's body, and highlighting of the digitized user movement of the at least one portion of the user's body in the display of the digitized user movement of the at least one portion of the user's body, wherein the highlights of the digitized user movement of the at least one portion of the user's body include a computer-generated display of at least one internal feature of the at least one portion of the user's body;

comparing, by the at least one processor, the acquired user data to predetermined historical user data and/or statistical norm data for other users to identify at least one anomaly in the user movement of the at least one portion of the user's body;

highlighting, by the at least one processor, the at least one anomaly in the user movement of the at least one portion of the user's body in the computer-generated version of the user movement of the at least one portion of the user's body; and providing, by the at least one processor, for display, using the signal, the highlights of the at least one anomaly in the user movement of the at least one portion of the user's body to provide interactive virtual care.

11. The method of claim 10, further comprising:

providing, by the at least one processor, for display a real-time version of the user movement of the at least one portion of the user's body adjacent to and/or superimposed on the computer-generated version of the user movement of the at least one portion of the user's body.

12. The method of claim 10, further comprising:

generating, by the at least one processor, metrics related to a degree of the at least one anomaly in the user movement of the at least one portion of the user's body.

13. The method of claim 10, further comprising:

providing, by the at least one processor, for display joints of the user's body as connectors and/or skeletal features of the user's body as line segments between the connectors in the computer-generated version of the user movement of the at least one portion of the user's body.

14. The method of claim 10, wherein the at least one sensory device comprises a video sensor to acquire a video stream of the user movement of the at least one portion of the user's body.

15. The method of claim 10, wherein the at least one sensory device comprises an audio sensor to acquire user data related to speech.

16. A non-transitory computer readable medium having stored thereon a computer executable program to provide interactive virtual care, the computer executable program when executed causes a computer system to:
   acquire, by at least one processor, user data related to user movement of at least one portion of a user's body by using a user sensory module comprising at least one sensory device, the user movement of the at least one portion of the user's body being performed at a distance away from the user sensory module;
   digitize, by the at least one processor, the user movement of the at least one portion of the user's body based on an interpretation of the acquired user data by the user sensory module;
   produce, by the at least one processor, a computer-generated version of the user movement of the at least one portion of the user's body;
   generate, by the at least one processor, a signal of the digitized user movement of the at least one portion of the user's body based on the interpretation of the acquired user data by the user sensory module and the computer-generated version of the user movement of the at least one portion of the user's body, wherein the signal is to provide for a display of the digitized user movement of the at least one portion of the user's body, and highlighting of the digitized user movement of the at least one portion of the user's body in the display of the digitized user movement of the at least one portion of the user's body;
   compare, by the at least one processor, the acquired user data to predetermined historical user data and/or statistical norm data for other users to identify at least one anomaly in the user movement of the at least one portion of the user's body, wherein the predetermined historical user data and the statistical norm data for the other users respectively include computer-generated versions of movements of the at least one portion of the user's body and movements of the same at least one portion of bodies of the other users;
   highlight, by the at least one processor, the at least one anomaly in the user movement of the at least one portion of the user's body in the computer-generated version of the user movement of the at least one portion of the user's body; and
   provide, by the at least one processor, for display, using the signal, the highlights of the at least one anomaly in the user movement of the at least one portion of the user's body to provide interactive virtual care.

17. The non-transitory computer readable medium of claim 16, the computer executable program when executed further causes the computer system to:
   provide, by the at least one processor, for display joints of the user's body as connectors and/or skeletal features of the user's body as line segments between the connectors in the computer-generated version of the user movement of the at least one portion of the user's body.

18. The non-transitory computer readable medium of claim 16, wherein the highlights of the digitized user movement of the at least one portion of the user's body include a computer-generated display of at least one internal feature of the at least one portion of the user's body.

19. The non-transitory computer readable medium of claim 16, wherein the at least one sensory device comprises a video sensor to acquire a video stream of the user movement of the at least one portion of the user's body.

20. The non-transitory computer readable medium of claim 16, wherein the at least one sensory device comprises an audio sensor to acquire user data related to speech.

* * * * *